United States Patent
Lane

(12) 
(10) Patent No.: US 10,667,687 B2
(45) Date of Patent: Jun. 2, 2020

(54) MONITORING SYSTEM FOR PHYSIOLOGICAL PARAMETER SENSING DEVICE

(71) Applicant: Welch Allyn, Inc., Skaneateles Falls, NY (US)

(72) Inventor: John A. Lane, Weedsport, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 284 days.

(21) Appl. No.: 15/479,840

(22) Filed: Apr. 5, 2017

(65) Prior Publication Data
US 2017/0344736 A1    Nov. 30, 2017

Related U.S. Application Data

(60) Provisional application No. 62/343,306, filed on May 31, 2016.

(51) Int. Cl.
| A61B 5/00 | (2006.01) |
| G06F 19/00 | (2018.01) |
| A61B 5/0205 | (2006.01) |
| A61B 5/0408 | (2006.01) |

(Continued)

(52) U.S. Cl.
CPC ............ A61B 5/0008 (2013.01); A61B 5/002 (2013.01); A61B 5/0006 (2013.01);
(Continued)

(58) Field of Classification Search
CPC ..... A61B 5/002; A61B 5/0006; A61B 5/0008; A61B 5/117; A61B 5/02055;
(Continued)

(56) References Cited

U.S. PATENT DOCUMENTS

| 6,477,424 B1 * | 11/2002 | Thompson ......... A61N 1/37217 |
| | | 607/60 |
| 6,577,901 B2 | 6/2003 | Thompson |
| | (Continued) | |

FOREIGN PATENT DOCUMENTS

| WO | 2014202445 A1 | 12/2014 |
| WO | WO-2014202445 A1 * | 12/2014 |
| WO | 2015006196 A1 | 1/2015 |

OTHER PUBLICATIONS

Schreiner, Bruce, "Convenient Wireless Connectivity with Tap and Connect", Retrieved on: Jul. 29, 2015, available at: http://www.engineering.com/ElectronicsDesign/ElectronicsDesignArticles/ArticleID/7527/Convenient-Wireless-Connectivity-with-Tap-and-Connect.aspx, Publication date: May 6, 2014, 11 pages.

(Continued)

*Primary Examiner* — Steven Lim
*Assistant Examiner* — Mancil Littlejohn, Jr.
(74) *Attorney, Agent, or Firm* — Merchant & Gould P.C.

(57) ABSTRACT

A system for detecting a physiological parameter of a subject includes a sensing device attached to a patient and an interrogation device for monitoring an operation of the sensing device. The interrogation device is used to interrogate the sensing device to confirm that the sensing device is in proper operation while being attached to the patient. The interrogation device further performs user authentication and determines a type and/or extent of information that can be presented on the interrogation device based on the level of user authentication.

20 Claims, 17 Drawing Sheets

(51) Int. Cl.
*G16H 10/60* (2018.01)
*G06F 21/62* (2013.01)
*A61B 5/117* (2016.01)

(52) U.S. Cl.
CPC ...... *A61B 5/02055* (2013.01); *A61B 5/04087* (2013.01); *G06F 19/324* (2013.01); *G06F 21/6245* (2013.01); *G16H 10/60* (2018.01); *A61B 5/117* (2013.01); *G06F 2221/2113* (2013.01); *G06F 2221/2153* (2013.01)

(58) Field of Classification Search
CPC .. A61B 5/04087; G16H 10/60; G06F 19/324; G06F 21/6245; G06F 2221/2113; G06F 2221/2153
See application file for complete search history.

(56) References Cited

U.S. PATENT DOCUMENTS

| | | | |
|---|---|---|---|
| 9,323,245 B2* | 4/2016 | Bush | G05B 23/0216 |
| 2007/0180047 A1* | 8/2007 | Dong | A61B 5/1171 |
| | | | 709/217 |
| 2012/0156933 A1 | 6/2012 | Kreger et al. | |
| 2012/0238216 A1 | 9/2012 | Hallowell et al. | |
| 2013/0331036 A1 | 12/2013 | Baker et al. | |
| 2014/0025809 A1* | 1/2014 | Steuperaert | H04L 67/12 |
| | | | 709/224 |
| 2014/0121557 A1 | 5/2014 | Gannon et al. | |
| 2014/0304773 A1* | 10/2014 | Woods | H04L 63/08 |
| | | | 726/3 |
| 2015/0050888 A1 | 2/2015 | Baker et al. | |
| 2015/0126118 A1 | 5/2015 | Lin et al. | |
| 2015/0164326 A1 | 6/2015 | Baker et al. | |
| 2016/0246989 A1* | 8/2016 | Roy | G06F 21/6245 |

OTHER PUBLICATIONS

Vazquez-Briseno et al., "Using RFID/NFC and QR-Code in Mobile Phones to Link the Physical and the Digital World", Retrieved on Jul. 29, 2015, available at: http://cdn.intechopen.com/pdfs-wm/31056.pdf, 25 pages.

* cited by examiner

MONITORING SYSTEM FOR PHYSIOLOGICAL PARAMETER SENSING DEVICE

CROSS-REFERENCE TO RELATED APPLICATION(S)

This application claims the benefit of U.S. Patent Application Ser. No. 62/343,306, titled MONITORING SYSTEM FOR PHYSIOLOGICAL PARAMETER SENSING DEVICE, filed May 31, 2016, the disclosure of which is hereby incorporated by reference in its entirety.

BACKGROUND

Wearable body sensors can be used to efficiently monitor physiological parameters or vital signs, such as body temperature or heartbeat, in various situations. Some examples of wearable body sensors are designed to remain attached to a patient body to periodically detect physiological parameters for certain period of time. While a body sensor is attached to the patient body, the body sensor can fail for various reasons. In some examples, the body sensor can be accidentally decoupled from the patient body, and therefore fails to detect a physiological parameter properly. The operating status of the body sensor is typically unknown until the body sensor is disengaged from the patient and the measurement data stored in the body sensor is retrieved and evaluated.

SUMMARY

In general terms, this disclosure is directed to a system for monitoring a physiological parameter. In one possible configuration and by non-limiting example, the system includes a physiological parameter sensing device and an interrogation device configured to monitor an operation of the sensing device. Various aspects are described in this disclosure, which include, but are not limited to, the following aspects.

One aspect is a system for monitoring a physiological parameter of a subject. The system includes a sensing device engaged to a subject and configured to measure a physiological parameter of the subject; and an interrogation device operable by a user and configured to: establish communication with the sensing device; receive data from the sensing device, the data including non-patient specific data; determine whether the user is authenticated; and present at least a portion of the non-patient specific data when the user is not authenticated.

Another aspect is an interrogation apparatus for monitoring an operation of a physiological parameter sensing device. The interrogation apparatus includes a processing device configured to control operation of the interrogation apparatus; a display device; and a computer readable data storage device storing software instructions that, when executed by the processing device, cause the interrogation apparatus to: establish communication with the sensing device; receive data from the sensing device, the data including non-patient specific data; determine whether the user is authenticated; and display at least a portion of the non-patient specific data using the display device when the user is not authenticated.

Yet another aspect is a method of monitoring an operation of a physiological parameter sensing device. The sensing device is configured to detect a physiological parameter of a subject. The method includes transmitting a trigger signal to the sensing device to activate the sensing device; establishing communication with the sensing device; providing a user interface configured to receive user authentication information; determining whether the user is authenticated; when the user is not authenticated, receiving non-patient specific data from the sensing device; and displaying at least a portion of the non-patient specific data using a display device; and when the user is authenticated, determining a level of authentication; receiving patient-specific data corresponding to the level of authentication; and displaying at least a portion of the patient specific data corresponding to the level of authentication.

DETAILED DESCRIPTION

Figure 1:
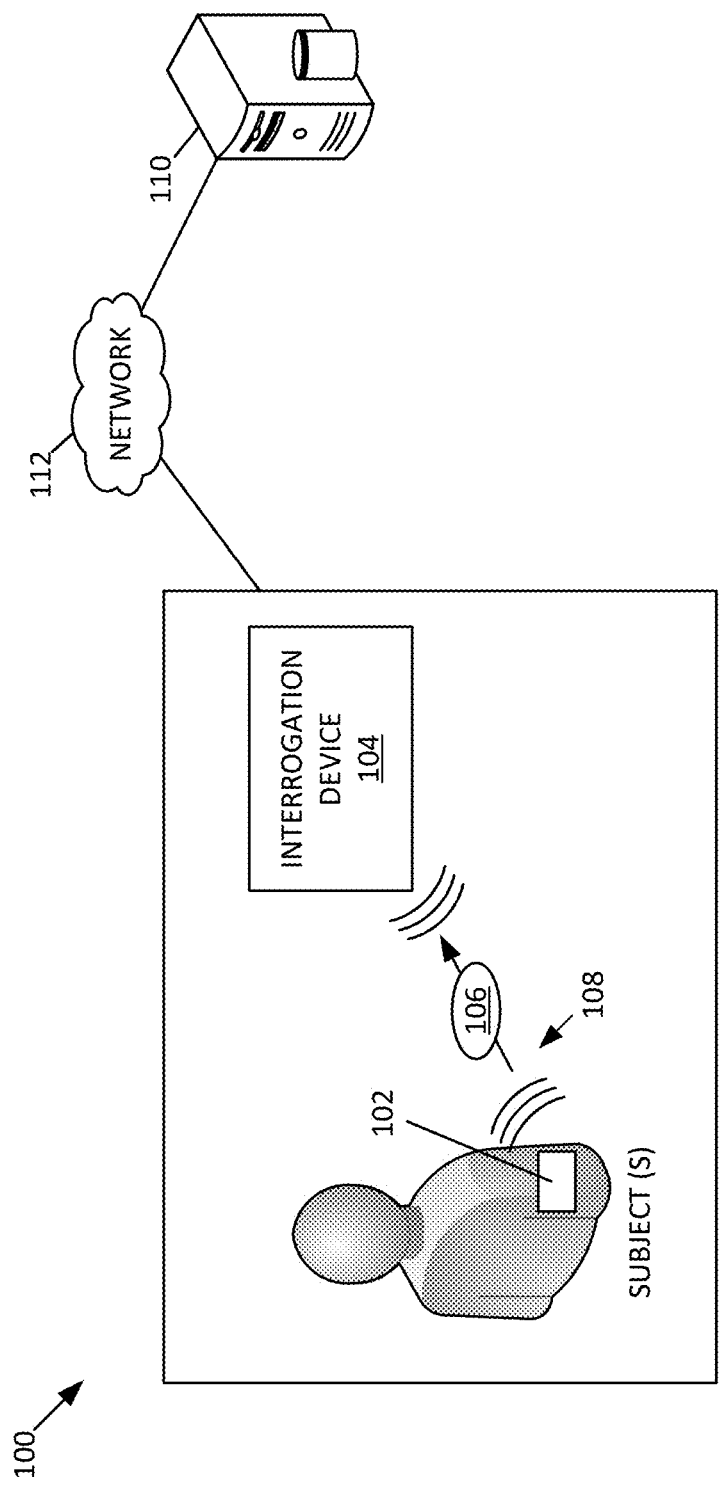
FIG. 1 schematically illustrates an example system for monitoring a physiological parameter using a physiological parameter sensing device.

Various embodiments will be described in detail with reference to the drawings, wherein like reference numerals represent like parts and assemblies throughout the several views.

In general, a system in accordance with the present disclosure operates to detect a physiological parameter of a subject using a sensing device, and monitor the operation of the sensing device using an interrogation device. For example, the system enables monitoring that the sensing device, such as a patch or other body-worn sensors, is working properly to acquire data during a monitoring period. The sensing device can be configured as a 24-hour monitoring device (e.g., patch) that is used for an extended period of time, such as a period of hours, one day, multiple days or weeks.

When a sensing device, such as a patch, is attached to and carried by a patient, the sensing device can fail for various reasons. For example, the sensing device can be decoupled from the patient during the monitoring period and thus fail to monitor a physiological parameter of the patient as programmed. By way of example, a coupling device, such as an adhesive layer, that attaches the body sensor to the patient is not reliable enough to maintain the body sensor in place. In another example, the electronics associated with the device could fail, which could lead to faulty or non-collection of data. Other types of failures can occur.

In these cases, the body sensor fails to detect a physiological parameter properly. The system of the present disclosure includes an interrogation device for obtaining status updates from the sensing device.

In some examples, such status information can be transmitted from the sensing device to the interrogation device when the interrogation device is held close to the sensing device. The proximity between the sensing device and the interrogation device can establish pairing between the sensing device and the interrogation device so that the sensing device is interrogated anytime during the monitoring period. When the interrogation device is paired up with the sensing device, the interrogation device can acquire information, such as a small window of data including, for example, a status bit of the sensing device (i.e., information about whether the sensing device is working properly) and a remaining battery power. In other examples, different communication methods can be utilized to monitor the operation of the sensing device using the interrogation device.

The interrogation device can be of various types, such as smartphones, tablets, wearable devices, or other independent devices, which can be used by the caregiver, patient or other individuals having an interest in the operation of the sensing device.

In some examples, the interrogation device is further configured to perform user authentication and determine a type and/or extent of information that can be presented on the interrogation device based on the level of user authentication. For example, the interrogation device provides a user interface for receiving authentication information for a user who operates the interrogation device and receives the user authentication information. The interrogation device determines a level of authentication based on the received user authentication information and displays different sets of information, which are transmitted from the sensing device and/or a patient data management system, depending on different levels of user authentication. As such, a user of the interrogation device can simply access minimal information about the sensing device, such as the operational status and/or the battery left in the sensing device, without user authentication. When the user is authenticated, the interrogation device can present additional information, such as measurement data obtained by the sensing device and/or patient record, to the user according to a level of authentication.

FIG. 1 schematically illustrates an example system 100 for monitoring a physiological parameter using a physiological parameter sensing device 102. The system 100 further operates to monitor an operation of the physiological parameter sensing device 102 using an interrogation device or apparatus 104. The physiological parameter sensing device 102 operates to detect one or more physiological parameters of a subject S. The interrogation device 104 is configured to communicate with the physiological parameter sensing device 102 and monitor the operation of the physiological parameter sensing device 102. In some examples, the interrogation device 104 receives sensing device data 106 from the physiological parameter sensing device 102. The physiological parameter sensing device 102 can communicate with the interrogation device 104 via a wireless communication link 108.

The physiological parameter sensing device 102 is worn or carried by the subject S. In some examples, the sensing device 102 includes a physiological parameter sensing patch. In this document, therefore, the sensing device 102 is also referred to as a physiological parameter sensing patch, a sensing patch, a monitoring patch, or the like.

In some examples, the sensing device 102 is removably attached to a portion of the subject's body or the subject's skin. The sensing device 102 can be worn on different locations of the subject body, such as the forehead, torso, neck, arm, leg, or other on-body locations, for different measurements. In other examples, the sensing device 102 is implanted to the subject's body. The sensing device 102 can be attached or implanted to the subject S by a healthcare practitioner when the healthcare practitioner sees the subject S. In other examples, the subject S can wear or attach the sensing device 102 on his or her own.

The sensing device 102 can remain attached to the subject S for an extend amount of time, such as days or weeks, in or outside the clinical environment (such as a clinic or hospital). For example, the subject S can wear the sensing device 102 in the subject's normal life for long term monitoring. In other examples, the sensing device 102 is used for a patient who is hospitalized.

The sensing device 102 operates to detect one or more physiological parameters of the subject S. The subject S can also be referred to herein as a patient or person. The sensing device 102 is configured to detect one or more physiological parameters. In some examples, the sensing device 102 includes one sensor unit to measure the same type of physiological parameters. In other examples, the sensing device 102 includes a plurality of sensor units of different types capable of detecting different kinds of physiological parameters. The sensing device 102 transmits signals to the interrogation device 104 via the wireless communication link 108.

Physiological parameters can include vital signs, physiological measurements, and biological measurements, which can be detected from various portions of the subject's body. For example, physiological parameters include measurements of the body's basic functions, which are useful in detecting or monitoring medical problems. Examples of physiological parameters include body temperature, pulse rate (i.e., heart rate), respiration rate (i.e., breathing rate), blood pressure, blood gas, and SpO2. Body temperature can be taken in various manners, such as orally, rectally, by ear, or by skin. The pulse rate is a measurement of the heart rate, or the number of times the heart beats per minute. The pulse rate can also indicate a heart rhythm and the strength of the pulse. The pulse can be taken on different body portions where the arteries are located, such as on the side of the neck, on the side of the elbow, or at the wrist. The respiration rate is the number of breaths a person takes per minute and is used to note whether the person has any difficulty breathing. Blood pressure is the force of the pushing against the artery walls. There may be other vital signs, such as pain, Glasgow coma scale, pulse oximetry, blood glucose level, end-tidal $CO_2$, functional status, shortness of breath, and gait speed.

By way of example, the sensing device 102 is configured to measure body temperature of the subject S. In other examples, the sensing device 102 can be configured to measure different physiological parameters, such as blood gas, SpO2, blood pressure, heart rate, and any other parameters, in addition to or in lieu of body temperature.

In yet other examples, the sensing device 102 is configured as an electrocardiography (ECG) patch. Electrocardiography is a process of recording electrical activity of the heart over a period of time. Such an ECG patch can be configured in various manners. In some examples, the ECG patch includes electrodes that are to be placed on a patient's body. These electrodes detect the tiny electrical changes on the skin that arise from the heart muscle depolarizing during each heartbeat. By way of example, electrodes can be placed on the patient's limbs and on the surface of the chest. The overall magnitude of electrical potential of the heart is then measured from different angles ("leads") and is recorded over a period of time. In this way, the overall magnitude and direction of electrical depolarization of the heart is captured at each moment throughout the cardiac cycle. An electrocardiogram can be generated, which is a graph of voltage versus time produced by the electrocardiography.

The ECG patch can be used for various purposes. In some examples, the ECG patch is used to measure the rate and rhythm of heartbeats, the size and position of the heart chambers, the presence of any damage to the heart's muscle cells or conduction system, the effects of cardiac drugs, and the function of implanted pacemakers. For example, the ECG sensing device can be used to monitor suspected heart attack, pulmonary embolism, a third heart sound, a fourth heart sound, a cardiac murmur or other findings to suggest structural heart disease, perceived cardiac dysrhythmias, fainting or collapse, and seizures. The ECG device can also be used to monitor the effects of a heart medication, assess severity of electrolyte abnormalities, such as hyperkalemia.

As described herein, the ECG patch can be continuously used for an extended period of time (e.g., days, weeks, or months). For example, such a continuous ECG patch monitors critically ill patients, patients undergoing general anesthesia, and patients who have an infrequently occurring cardiac dysrhythmia that would be unlikely to be seen on a conventional ECG which is used for a short period of time (e.g., a few seconds).

With continued reference to FIG. 1, the interrogation device 104 is used to detect an operation status of the sensing device 102. The interrogation device 104 can be used to make sure that the sensing device 102 operates to monitor physiological parameters as programmed, such as continuous or periodic monitoring.

The interrogation device 104 can be operated by any person. In some examples, the subject S who wears the sensing device 102 can use the interrogation device 104 to ensure that the sensing device 102 is in proper operation. In other examples, the interrogation device 104 is used by any other person, such as a guardian and a healthcare practitioner, to confirm the operation of the sensing device 102. The guardian is a person or a group of people who are interested in the health conditions of the subject S. Examples of the guardian include a parent of the subject S, a family member of the subject S, a caregiver of the subject S, a primary physician of the subject S, and any other interested parties.

The healthcare practitioner is a person who provides healthcare service to the subject S. Examples of healthcare practitioners P include primary care providers (e.g., doctors, nurse practitioners, and physician assistants), nursing care providers (e.g., nurses), specialty care providers (e.g., professionals in various specialties), and health professionals that provide preventive, curative, promotional and rehabilitative health care services. The healthcare practitioner can be an institution, company, business, and/or entity. In this document, such people who can use the interrogation device 104 in connection with the sensing device 102 can be collectively referred to as a user.

The interrogation device 104 operates to communicate with the sensing device 102 attached to the subject S. In some examples, the interrogation device 104 is operated to establish communication with the sensing device 102 and monitor the operational status of the sensing device 102 as needed. For example, the user can use the interrogation device 104 when the user wants to confirm that the interrogation device 104 is working properly. As described below, the interrogation device 104 can be brought close to the sensing device 102 to establish communication therebetween and receive data (including information about the operational status of the sensing device 102) from the sensing device 102. In other examples, the interrogation device 104 is configured to either continuously or periodically monitor the operational status of the sensing device 102.

The interrogation device 104 can be of various configurations. In some examples, the interrogation device 104 is an electronic device or computing device dedicated for particular sensing devices 102. In other examples, other consumer level computing devices can be used for the interrogation device 104. Such computing devices can include a mobile computing device, such as a smartphone, (e.g., an iPhone, an Android operating phone, a Blackberry, a Window operating phone, etc.); a tablet computer (e.g., an iPad), and a personal digital assistant (PDA). The interrogation device 104 can include a desktop computer, a laptop computer, and/or any other suitable devices operable to send and receive signals, store and retrieve data, and/or execute modules.

In some examples, the interrogation device 104 is configured as a portable reader. Such a portable interrogation device 104 can be configured as an independent handheld device, or as a device that is connected to a movable clinical data station or equipment. As described herein, for home care, the interrogation device 104 can be various consumer mobile devices as described above. In other examples, the interrogation device 104 is mounted to a structure or device that a user uses periodically or continuously. For example, the interrogation device 104 is mounted to the sides or side rails of a hospital or homecare bed for a patient, such that the interrogation device 104 remains within, or easily comes into, a read range of the sensing device 102 attached to the patient's body. The interrogation device 104 can also be included in a headboard or control system of the hospital bed. In yet other examples, the interrogation device 104 is incorporated into, or used with, other monitoring systems, such as Connex® Vital Signs Monitor (CVSM) available from Welch Allyn Inc., Skaneateles Falls, N.Y. An example of the interrogation device 104 is described in more detail with reference to FIG. 6.

The interrogation device 104 can receive signals from the sensing device 102 via the wireless communication link 108. In some examples, the interrogation device 104 is operable to present the data transmitted from the sensing device 102 thereon. For example, the interrogation device 104 includes a user interface (e.g., a display screen) and operates to present the transmitted data on the screen in a visible format. Alternatively, the interrogation device 104 can output the data in an audible format, and/or provide an alert in visible and/or audible manners.

The sensing device data 106 can include data stored in the sensing device 102. At least a portion of the sensing device data 106 can be transmitted to the interrogation device 104 and presented to the user of the interrogation device 104. An example of the sensing device data 106 is described in more detail with reference to FIG. 4.

As illustrated in FIG. 1, the wireless communication link 108 is established between the sensing device 102 and the interrogation device 104. At least a portion of data (e.g., the sensing device data 106) stored in the sensing device 102 is wirelessly transmitted to the interrogation device 104 via the wireless communication link 108. The wireless communication link 108 can be established as short range wireless communication, such as radio frequency identification (RFID) communication, near field communication (NFC), Bluetooth communication, or Wi-Fi communication.

In some examples, the interrogation device 104 is configured as an active RFID reader and capable of communicating with the sensing device 102, which correspondingly includes a RFID device (e.g., a RFID tag). When the interrogation device 104 is brought close enough to the sensing device 102 attached to the subject S, a short-range RF communication is established between the sensing device 102 and the interrogation device 104 via electromagnetic fields so that query, authorization/authentication, and/or data interchange processes are performed between the sensing device 102 and the interrogation device 104.

In other examples, the interrogation device 104 includes a NFC interface for establishing radio communication with the sensing device 102 by bringing the interrogation device 104 into proximity to the sensing device 102 or touching the interrogation device 104 with the sensing device 102. The NFC interface can be configured in a way known in the art. The sensing device 102 is correspondingly configured to communicate with the NFC interface of the interrogation device 104. As such, the interrogation device 104 operates as an NFC reader and the sensing device 102 functions as an NFC tag.

In yet other examples, the interrogation device 104 includes a Bluetooth communication interface to establish Bluetooth wireless connection with the sensing device 102. The Bluetooth communication interface can be configured in a way known in the art. The sensing device 102 is also configured to be capable of establish Bluetooth communication with the interrogation device 104. As such, the sensing device 102 and the interrogation device 104 can be correspondingly configured to transmit data via low-power radio waves.

In yet other examples, the interrogation device 104 includes a Wi-Fi communication interface to establish Wi-Fi connection with the sensing device 102. The Wi-Fi communication interface can be designed in a way known in the art. The sensing device 102 is also configured to communicate with the Wi-Fi communication interface of the interrogation device 104. As such, the sensing device 102 and the interrogation device 104 can be correspondingly configured to transmit data via radio waves. By way of non-limiting example, and as will be appreciated by those skilled in the relevant arts, Wi-Fi can be deployed in accordance with IEEE 802.11 (Wireless LAN), IEEE 802.15.4 (Low-Rate wireless PAN, such as ZigBee, WirelessHART, and MiWi), IEEE 802.22 (Wireless Regional Area Network), or other standard. In some embodiments, Wi-Fi connection can be alternatively established if other connections (e.g., RFID, NFC, and Bluetooth) are not established.

In other embodiments, the wireless communication link 108 can implement other types of short-range communications, such as infrared data communication, Z-Wave, ANT+, and other suitable protocols.

Although the wireless communication link 108 is primarily described in the present disclosure, other embodiments are also possible where a wired communication link replaces the wireless communication link 108 or used together with the wireless communication link 108.

As such, since the sensing device 102 and the interrogation device 104 communicate with each other via the wireless communication link 108, the system 100 allows conveniently monitoring whether the sensing device 102 is in operation as programmed to measure physiological parameters of the subject S. For example, when the subject S wears the sensing device 102, a user of the interrogation device 104 can simply bring the interrogation device 104 close to the sensing device 102 and obtain from the sensing device 102 data that contains information about the operational status of the sensing device 102.

With continued reference to FIG. 1, in some examples, the sensing device monitoring system 100 is operable to communicate with a data management system 110 via a data communication network 112. The data management system 110 operates to manage the subject's personal and/or medical information, such as health conditions and other information. The data management system 110 can be operated by the healthcare practitioner and/or a healthcare service provider, such as a hospital or clinic.

Some embodiments of the data management system 110 are configured to communicate with either or both of the sensing device 102 and the interrogation device 104. For example, the interrogation device 104 and the data management system 110 are connected via the network 112 to transmit various data therebetween. In other examples, the sensing device 102 is capable of directly communicating with the data management system 110 to transmit measurement data (and other data associated with the subject S). In some examples, the data management system 110 operates to provide information that can be used to assist the subject S, the guardian and/or the healthcare practitioner to provide suitable healthcare to the subject S. In some examples, the data management system 110 includes such a computing device as described in FIG. 7. Examples of the data management system 110 include Connex® data management systems available from Welch Allyn Inc., Skaneateles Falls, N.Y.

The data communication network 112 communicates digital data between one or more computing devices, such as among the sensing device 102, the interrogation device 104, and the data management system 110. Examples of the network 112 include a local area network and a wide area network, such as the Internet. In some embodiments, the network 112 includes a wireless communication system, a wired communication system, or a combination of wireless and wired communication systems. A wired communication system can transmit data using electrical or optical signals in various possible embodiments. Wireless communication systems typically transmit signals via electromagnetic waves, such as in the form of optical signals or radio frequency (RF) signals. A wireless communication system typically includes an optical or RF transmitter for transmitting optical or RF signals, and an optical or RF receiver for receiving optical or RF signals. Examples of wireless communication systems include Wi-Fi communication devices (such as utilizing wireless routers or wireless access points), cellular communication devices (such as utilizing one or more cellular base stations), and other wireless communication devices.

Figure 2:
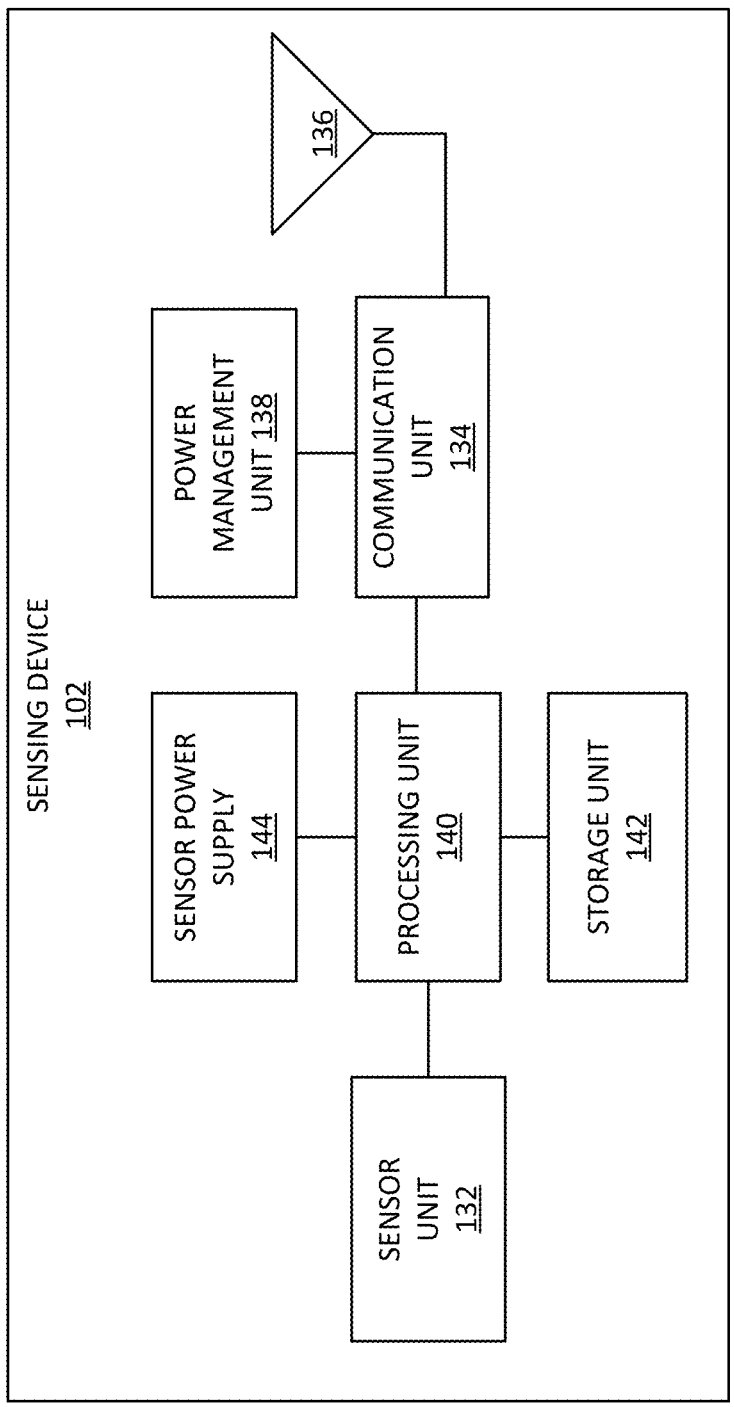
FIG. 2 schematically illustrates an example of the sensing device of FIG. 1.

FIG. 2 schematically illustrates an example of the sensing device 102, which is used to measure physiological parameters of the subject S. In the illustrated example, the sensing device 102 includes a sensor unit 132, a communication unit 134, an antenna 136, a power management unit 138, a processing unit 140, a storage unit 142, and a sensor power supply 144. In other embodiments, the sensing device 102 can include one or more components in addition to the components described above, and/or replace one or more of the components described above by different components. In some examples, the sensing device 102 is at least partially implemented in an integrated circuit.

The sensor unit 132 includes one or more sensors operable to detect one or more physiological parameters. In some examples, the sensor unit 132 includes one sensor for detecting one type of physiological parameters. In other examples, the sensor unit 132 includes a plurality of sensors for detecting different types of physiological parameters. Example sensors of the sensor unit 132 include temperature sensors, heartrate sensors, electrocardiogram (ECG) sensors, respiratory rate sensors, accelerometers, SpO2 sensors, heartrate variability sensors, galvanic skin response sensors, blood pressure sensors, blood glucose sensors, blood oxygen sensors, and any other sensors suitable for measuring physiological parameters. The sensor unit 132 can further include one or more sensors (e.g., accelerometer) for detecting the subject's activity and posture, such as whether the subject is standing, sitting, laying down, or engaged in physical activity, such as running. In some examples, the sensor unit 132 is powered by the sensor power supply 144.

The communication unit 134 operates to communicate with the interrogation device 104. In some examples, the communication unit 134 can receive signals from the interrogation device 104 via the wireless communication link 108 and transmit data (e.g., sensing device data 106) to the interrogation device 104. For example, the communication unit 134 can operate as a transponder configured to emit an identifying signal in response to an interrogating received signal from the interrogation device 104. The communication unit 134 is configured as an interface suitable for communicating with the interrogation device 104, such as near field communication (NFC), radio frequency identification (RFID), Bluetooth, Wi-Fi, and other short-range wireless communications. In other examples, the communication unit 134 is further configured to communicate with the data management system 110 and/or other computing devices via the network 112.

The antenna 136 is configured to receive and transmit a radio frequency (RF) signal. In some examples, the antenna 136 is made flat so as to be incorporated into the sensing device 102. Other configurations are also possible in other embodiments.

The power management unit (PMU) 138 operates to harvest raw RF power received via the antenna 136. In particular, an RF wave received via the antenna 136 is transmitted to the PMU 138 as a signal. The signal is used for harvesting the power and also decoded for further processes. The sensing device 102 then use the power to respond as necessary in response to the incoming signal from the interrogation device 104.

In some examples, in the communication between the sensing device 102 and the interrogation device 104, the sensing device 102 operates as a passive NFC device. In this configuration, the sensing device 102 does not consumer power from internal power source, such as the sensor power supply 144, for communication with the interrogation device 104. Instead, when interrogated by the interrogation device 104, the sensing device 102 can be powered by electromagnetic induction from magnetic fields produced near the interrogation device 104. However, it is recognized that, during the communication with the interrogation device 104, the sensing device 102 can be powered in different manners.

The processing unit 140 operates to control the sensor unit 132 and other components in the sensing device 102. Further, the processing unit 140 operates to communicate with the interrogation device 104. In some examples, the processing unit 140 receives signals from the antenna 136. In some examples, a demodulator is provided to demodulate an RF signal received via the antenna 136. The demodulator can be implemented in a way known in the art, including, for example, attenuator stage and amplifier stage. The processing unit 140 can perform various operations and generate an output signal for transmission. In some examples, a modulator is provided to modulate an output signal generated by the processing unit 140. The modulated signal is transmitted through the antenna 136 to the interrogation device 104. The modulator can be implemented in a way known in the art, including, for example, driver stage and amplifier stage. The processing unit 228 can be implemented in a way known in the art, including, for example, a processor, a decoder, and an encoder.

The storage unit 142 includes one or more memories configured to store the sensing device data 106. As described herein, the sensing device data 106 can contain physiological parameter data obtained from the sensor unit 132 and other data associated with the sensing device 102 and/or the subject S. The sensing device data 106 is further described with respect to FIG. 4. At least a portion of the sensing device data 106 is transmitted to and readable by the interrogation device 104. The storage unit 142 can be of various types, including volatile and nonvolatile, removable and non-removable, and/or persistent media. In some embodiments, the storage unit 142 is an erasable programmable read only memory (EPROM).

The sensor power supply 144 is included in the sensing device 102 and provides power to operate the sensor unit 132 and associated elements, such as the processing unit 140 and the storage unit 142. In some examples, the sensor power supply 144 includes one or more batteries, which is either for single use or rechargeable.

Figure 3:
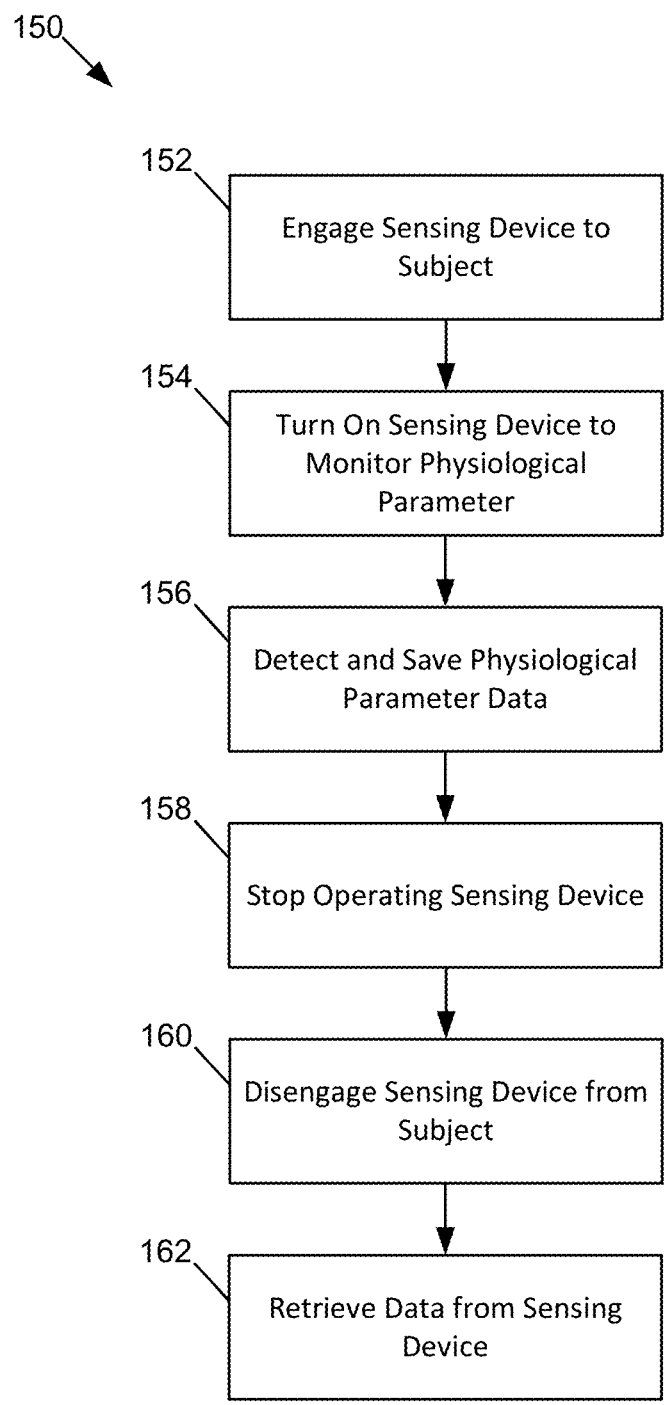
FIG. 3 is a flowchart illustrating an example method for measuring physiological parameters from a subject using the sensing device.

FIG. 3 is a flowchart illustrating an example method 150 for measuring physiological parameters from the subject S using the sensing device 102.

In the present disclosure, the sensing device 102 includes a body-worn device, such as a patch, at least a portion of which is removably attached on the body surface of the subject S and configured to monitor one or more physiological parameters of the subject S as described above.

At operation 152, the sensing device 102 is engaged with the subject S. In some examples, the sensing device 102 is configured to measure physiological parameters of the subject for a monitoring period of time. Such a monitoring period of time varies for different purposes. In some examples, the monitoring period of time is relatively short, such as for hours or less. In other examples, the monitoring period of time is extended to more than a day, such as days or weeks. A further extended monitoring period is also possible. By way of example, when a patient visits a healthcare practitioner, the practitioner can attach the sensing device 102 to a desirable location of the patient.

At operation 154, the sensing device 102 is turned on to monitor physiological parameters once engaged with the subject. The sensing device 102 will remain in operation during the monitoring period of time. For example, once the healthcare practitioner attaches the sensing device 102 to the subject S, the healthcare practitioner turns on the sensing device 102. The sensing device 102 remains in use so as to operate to measure physiological parameters as programmed.

The subject S with the sensing device 102 attached can be discharged or dismissed from the clinical environment while the sensing device 102 remains in operation to measure physiological parameters over the preset monitoring period of time. In other examples, the subject S with the sensing device 102 can be hospitalized while the sensing device 102 is in operation.

At operation 156, the sensing device 102 operates to detect physiological parameters from the subject S and save the parameters therein. In some examples, the sensing device 102 is activated periodically to obtain measurements over the monitoring period of time. In other examples, the sensing device 102 runs continuously to measure parameters of the subject. The monitoring schedule may be programmable so that the sensing device 102 can operate with different monitoring schedules.

At operation 158, the sensing device 102 stops operating after the programmed monitoring period of time. The sensing device 102 can be either manually or automatically turned off.

At operation 160, the sensing device 102 can be disengaged from the subject S. In some examples, the subject can visit the healthcare practitioner and the healthcare practitioner can remove the sensing device 102 from the subject. In other examples, the subject can detach the sensing device 102 on its own.

At operation 162, the sensing device 102 is connected to a computing device to retrieve the data saved in the sensing device 102. For example, the healthcare practitioner can connect the sensing device 102, either wirelessly or in wire, to a computer device, such as the data management system 110, and download data from the sensing device 102. The data may contain the physiological parameters measured by the sensing device 102 during the monitoring period of time.

Figure 4:
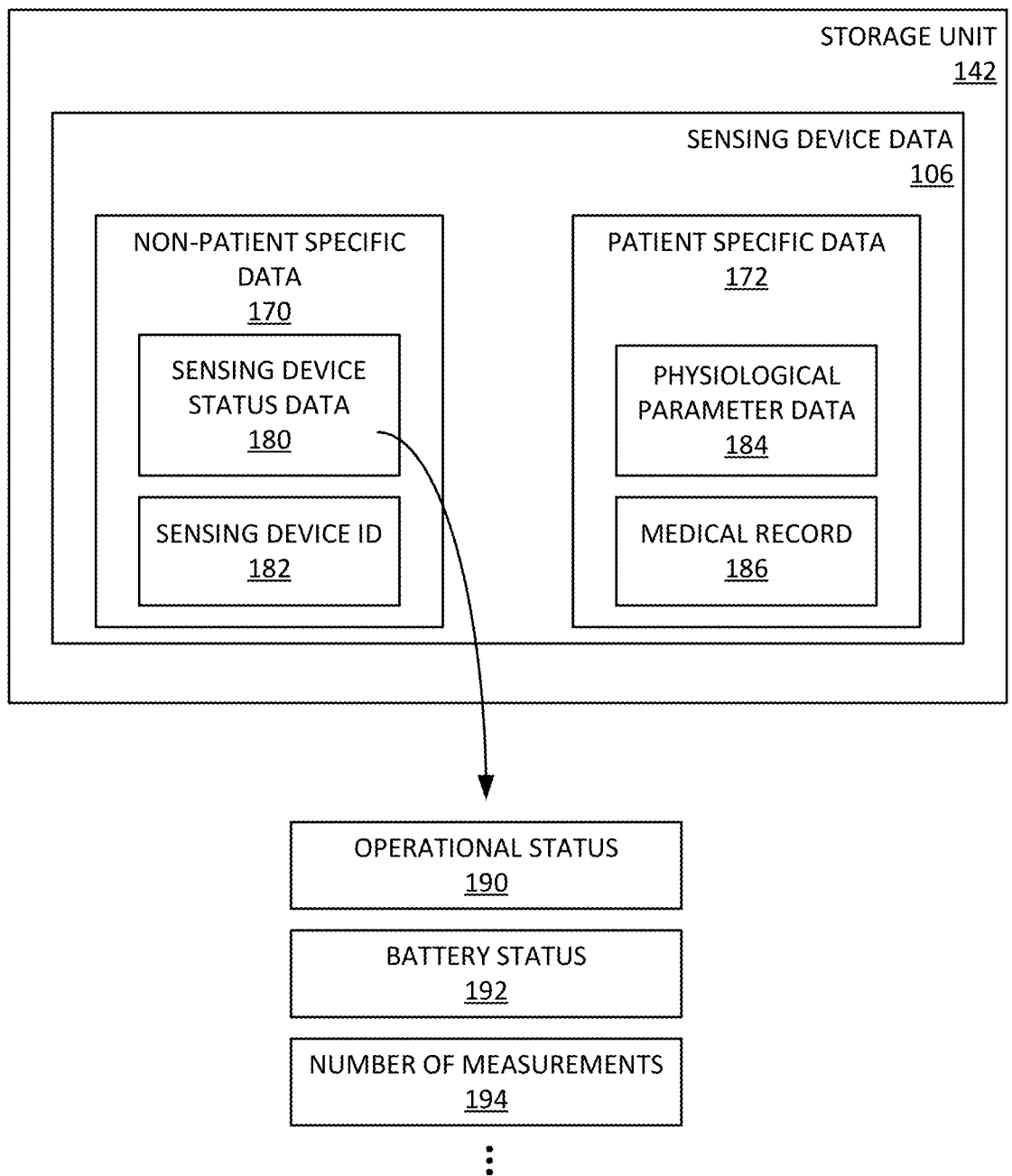
FIG. 4 illustrates an example of sensing device data.

FIG. 4 illustrates an example of the sensing device data 106. In the illustrated example, the sensing device data 106 is stored in the storage unit 142 of the sensing device 102. In some examples, the sensing device data 106 includes non-patient specific data 170 and patient specific data 172.

The non-patient specific data 170 includes information that is irrelevant, or little relevant, to the subject S that is monitored by the sensing device 102. The non-patient specific data 170 includes information that does not identify, contact, or locate the subject S on its own or with other information.

In some example, the non-patient specific data 170 includes sensing device status data 180 and sensing device identification data 182.

The sensing device status data 180 includes information about operational status of the sensing device 102. Some examples of the status data 180 include information about operation status 190, battery status 192, and a number of measurements 194. The operation status 190 indicates whether the sensing device 102 remains in operation as programmed. The battery status 192 indicates a level of battery remaining in the sensing device 102. The number of measurements 194 indicates the number of measurements or readings performed and/or obtained by the sensing device 102 for a particular period of time. Such a particular period of time can vary, such as a time period from the sensing device 102 is turned on to the current time, or a time period between two different points of time.

The sensing device identification data 182 includes information for identifying the sensing device 102, such as serial information or tag information. When the sensing device 102 is connected to the interrogation device 104, the device identification information can be transmitted to the interrogation device 104 for identifying the sensing device 102 in communication.

The patient specific data 172 includes information that can be used on its own or with other information to identify, contact, or locate the subject S. The patient specific data 172 may include private and/or confidential information about the subject S, which the subject S does not want to be shared without the subject's permission. In some examples, the patient specific data 172 includes personally identifiable information (PII) or sensitive personal information (SPI). For example, the patient specific data 172 includes any information about the subject, which can be used to distinguish or trace the subject's identity, such as name, address, email address, social security number, date, and place of birth, or biometric records, and any other information that is linked to the subject, such as medical, educational, financial, and employment information.

In some examples, the patient specific data 172 includes physiological parameter data 184 and patient record data 186. The physiological parameter data 184 includes information about physiological parameters of the subject S measured by the sensing device 102. The patient record data 186 includes the subject's personal information and medical history and care across time. In some examples, the patient specific data 172 can be transmitted from the data management system 110.

As described below, when the interrogation device 104 interacts with the sensing device 102, the type and/or extent of information that is retrieved from the sensing device data 106 and shared with the interrogation device 104 are different according to the level of user authentication. In general, at least a portion of the non-patient specific data 170 can be transmitted to, and presented on, the interrogation device 104 without authenticating a user of the interrogation device 104 or with a low level of the authentication.

Figure 5:
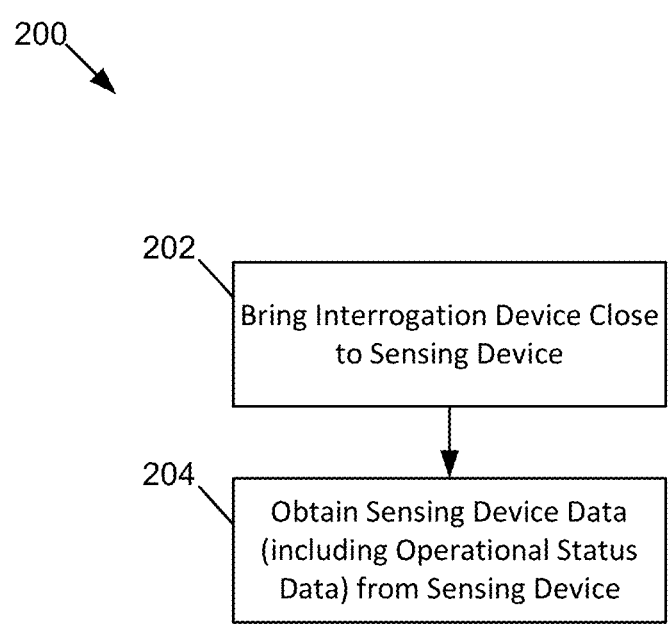
FIG. 5 is a flowchart illustrating an example method of monitoring the sensing device using an interrogation device.

FIG. 5 is a flowchart illustrating an example method 200 of monitoring the sensing device 102 using the interrogation device 104. At operation 202, the interrogation device 104 is brought close to the sensing device 102 within a predetermined communication range so that the sensing device 102 establishes communication with the interrogation device 104. Where the interrogation device 104 is configured as a passive device, the interrogation device 104 transmits a trigger signal to the sensing device 102 such that the sensing device 102 is supplied with electric power for activation.

At operation 204, once the communication establishes, the sensing device 102 transmits at least a portion of the sensing device data 106 (including the operation status data) to the interrogation device 104. The interrogation device 104 obtains the sensing device data 106 and presents the transmitted data in accordance with a level of authentication (or no authentication) for the user of the interrogation device 104.

Figure 6:
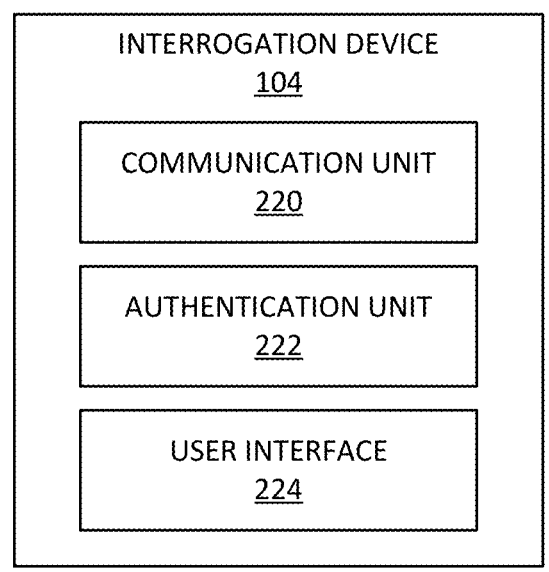
FIG. 6 is a block diagram that illustrates an example of the interrogation device of FIG. 5.

FIG. 6 is a block diagram that illustrates an example of the interrogation device 104. In the illustrated example, the interrogation device 104 includes a communication unit 220, an authentication unit 222, and a user interface 224.

The communication unit 220 operates to communicate with the sensing device 102 to transmit signals to, and receive data (e.g., the sensing device data 106) from, the sensing device 102. In some examples, the communication unit 220 uses the wireless communication link 108 to interact with the sensing device 102. An example of the communication is described above.

The authentication unit 222 operates to authenticate a user of the interrogation device 104. In some examples, the authentication unit 222 determines a level of authentication. The level of authentication is used to determine a type and/or extent of information that is selected from the sensing device data 106 and presented on the interrogation device 104. An example method of authentication is described in more detail with reference to FIG. 10.

The user interface 224 provides an interface through which a user of the interrogation device 104 provides user inputs to the interrogation device 104, and on which data is presented to the user. In some examples, the user interface 224 includes a display screen on which the data transmitted from the sensing device 102 is displayed. Examples of the user interface 224 are illustrated with reference to FIGS. 12-17.

Figure 7:
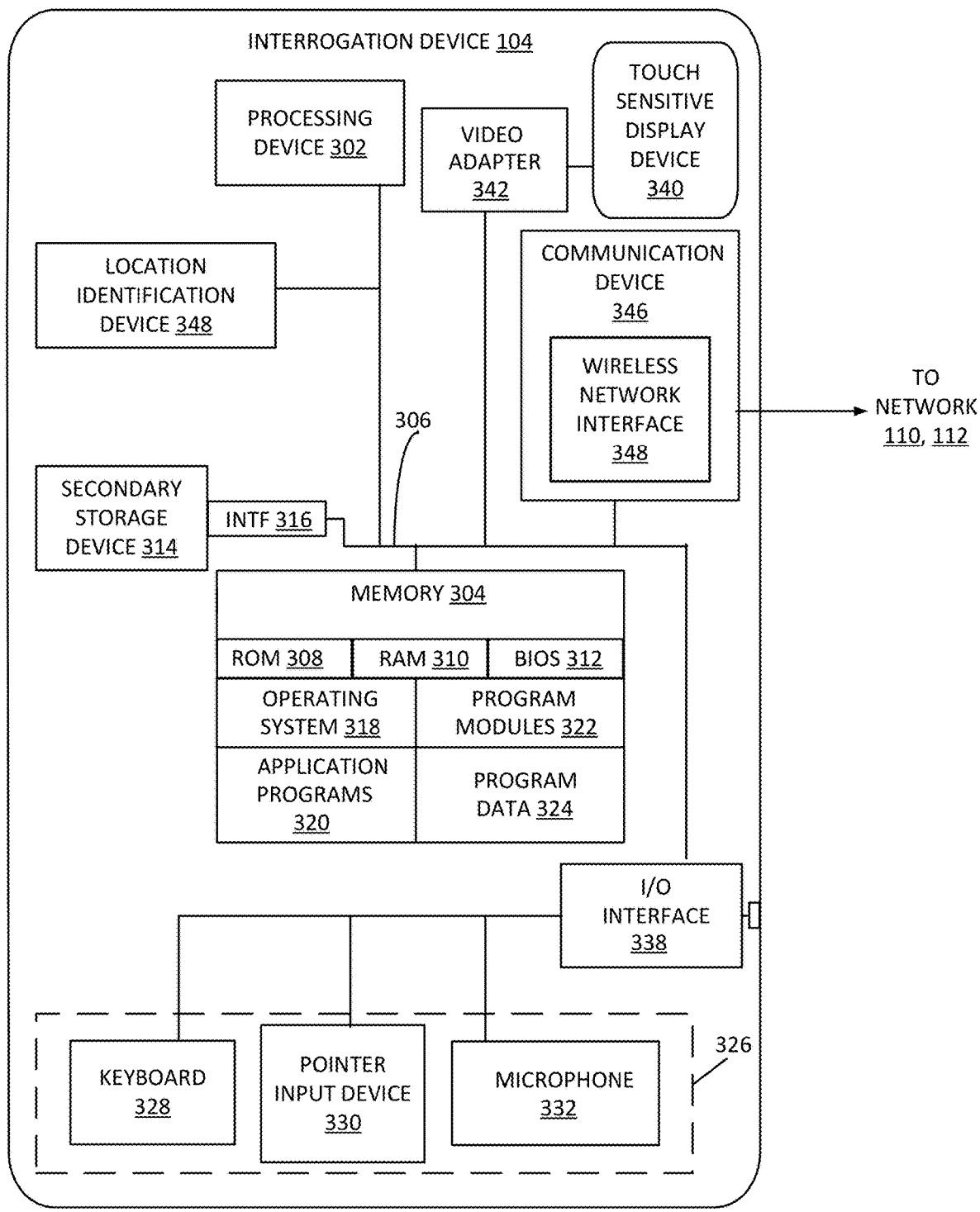
FIG. 7 illustrates an exemplary architecture of the interrogation device.

FIG. 7 illustrates an exemplary architecture of the interrogation device 104. The interrogation device 104 illustrated in FIG. 7 is used to execute the operating system, application programs, and software modules (including the software engines) described herein.

The interrogation device 104 is a computing device of various types. In some embodiments, the interrogation device 104 is a mobile computing device. Examples of the interrogation device 104 as a mobile computing device include a mobile device (e.g., a smart phone and a tablet computer), a wearable computer (e.g., a smartwatch and a head-mounted display), a personal digital assistant (PDA), a handheld game console, a portable media player, a ultra-mobile PC, a digital still camera, a digital video camera, and other mobile devices. In other embodiments, the interrogation device 104 is other computing devices, such as a desktop computer, a laptop computer, or other devices configured to process digital instructions. As described above, the interrogation device can also be a smart bed type system with electronics embedded in a headboard or control system of a hospital bed.

It is recognized that the architecture illustrated in FIG. 7 can also be implemented in other computing devices used to achieve aspects of the present disclosure. For example, the data management system 110 can be configured similarly to the architecture of FIG. 7. To avoid undue repetition, this description of the interrogation device 104 will not be separately repeated herein for each of the other computing devices including the data management system 110.

The interrogation device 104 includes, in some embodiments, at least one processing device 302, such as a central processing unit (CPU). A variety of processing devices are available from a variety of manufacturers, for example, Intel or Advanced Micro Devices. In this example, the interrogation device 104 also includes a system memory 304, and a system bus 306 that couples various system components including the system memory 304 to the processing device 302. The system bus 306 is one of any number of types of bus structures including a memory bus, or memory controller; a peripheral bus; and a local bus using any of a variety of bus architectures.

The system memory 304 includes read only memory 308 and random access memory 310. A basic input/output system 312 containing the basic routines that act to transfer information within the interrogation device 104, such as during start up, is typically stored in the read only memory 308.

The interrogation device 104 also includes a secondary storage device 314 in some embodiments, such as a hard disk drive, for storing digital data. The secondary storage device 314 is connected to the system bus 306 by a secondary storage interface 316. The secondary storage devices and their associated computer readable media provide nonvolatile storage of computer readable instructions (including application programs and program modules), data structures, and other data for the interrogation device 104.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device 314 or memory 304, including an operating system 318, one or more application programs 320, other program modules 322, and program data 324.

In some embodiments, the interrogation device 104 includes input devices to enable a user to provide inputs to the interrogation device 104. Examples of input devices 326 include a keyboard 328, a pointer input device 330, a microphone 332, and a touch sensitive display 340. Other embodiments include other input devices. The input devices are often connected to the processing device 302 through an input/output interface 338 that is coupled to the system bus 306. These input devices 326 can be connected by any number of input/output interfaces, such as a parallel port, serial port, game port, or a universal serial bus. Wireless communication between input devices and interface 338 is possible as well, and includes infrared, BLUETOOTH® wireless technology, 802.11a/b/g/n, cellular, or other radio frequency communication systems in some possible embodiments.

In this example embodiment, a touch sensitive display device 340 is also connected to the system bus 306 via an interface, such as a video adapter 342. The touch sensitive display device 340 includes touch sensors for receiving input from a user when the user touches the display. Such sensors can be capacitive sensors, pressure sensors, or other touch sensors. The sensors not only detect contact with the display, but also the location of the contact and movement of the contact over time. For example, a user can move a finger or stylus across the screen to provide written inputs. The written inputs are evaluated and, in some embodiments, converted into text inputs.

In addition to the display device 340, the interrogation device 104 can include various other peripheral devices (not shown), such as speakers or a printer.

The computing device 300 further includes a communication device 346 configured to establish communication across the network. In some embodiments, when used in a local area networking environment or a wide area networking environment (such as the Internet), the computing device 300 is typically connected to the network through a network interface, such as a wireless network interface 348. Other possible embodiments use other wired and/or wireless communication devices. For example, some embodiments of the computing device 300 include an Ethernet network interface, or a modem for communicating across the network. In yet other embodiments, the communication device 346 is capable of short-range wireless communication. Short-range wireless communication is one-way or two-way short-range to medium-range wireless communication. Short-range wireless communication can be established according to various technologies and protocols. Examples of short-range wireless communication include a radio frequency identification (RFID), a near field communication (NFC), a Bluetooth technology, and a Wi-Fi technology.

The interrogation device 104 typically includes at least some form of computer-readable media. Computer readable media includes any available media that can be accessed by the interrogation device 104. By way of example, computer-readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the interrogation device 104. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 7 is also an example of programmable electronics, which may include one or more such computing devices, and when multiple computing devices are included, such computing devices can be coupled together with a suitable data communication network so as to collectively perform the various functions, methods, or operations disclosed herein.

Referring again to FIG. 7, the interrogation device 104 can include a location identification device 348. The location identification device 348 is configured to identify the location or geolocation of the interrogation device 104. The location identification device 348 can use various types of geolocating or positioning systems, such as network-based systems, handset-based systems, SIM-based systems, Wi-Fi positioning systems, and hybrid positioning systems. Network-based systems utilize service provider's network infrastructure, such as cell tower triangulation. Handset-based systems typically use the Global Positioning System (GPS). Wi-Fi positioning systems can be used when GPS is inadequate due to various causes including multipath and signal blockage indoors. Hybrid positioning systems use a combination of network-based and handset-based technologies for location determination, such as Assisted GPS.

Figure 8:
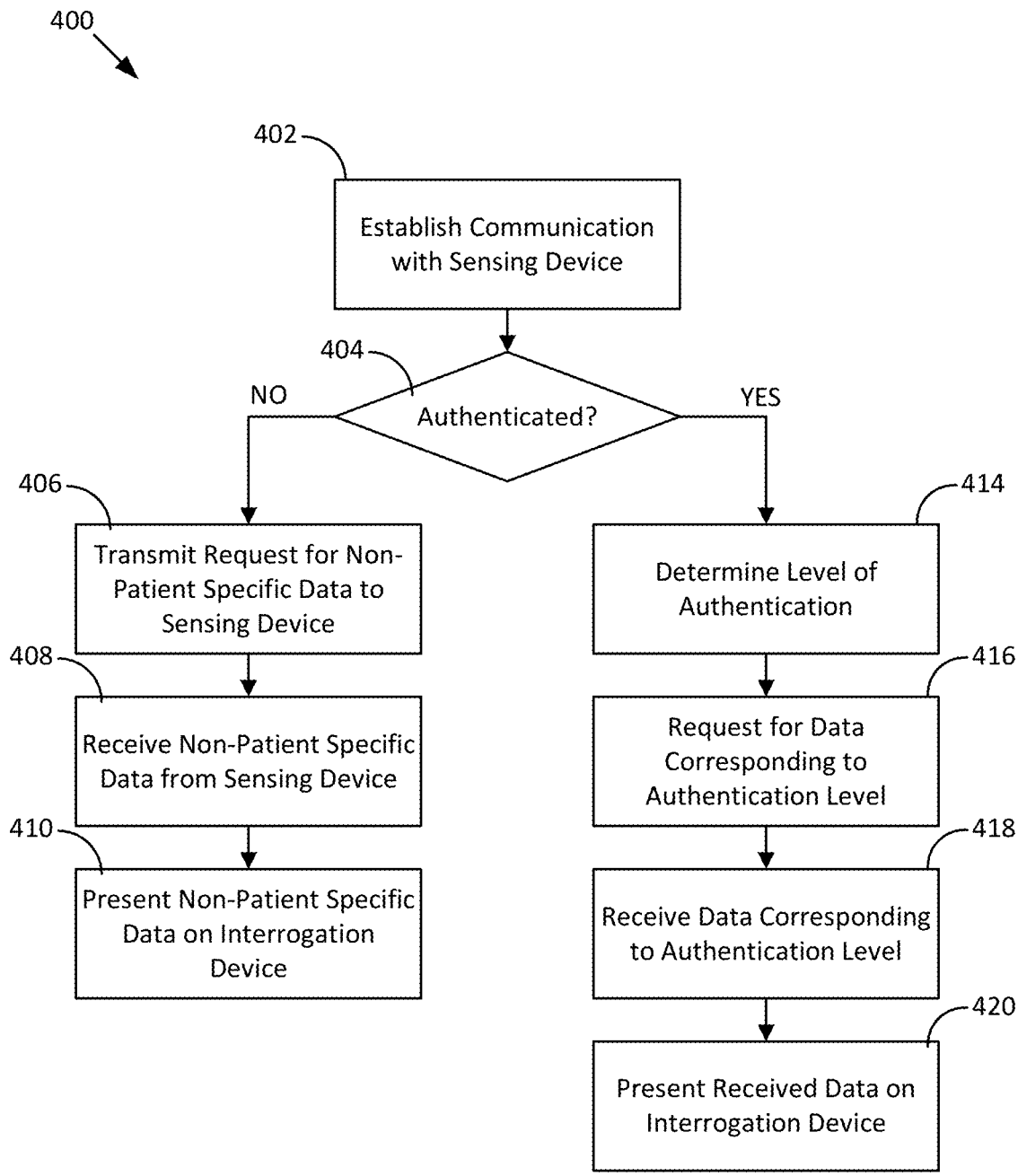
FIG. 8 is a flowchart illustrating an example method of operating the interrogation device in connection with the sensing device.

FIG. 8 is a flowchart illustrating an example method 400 of operating the interrogation device 104 in connection with the sensing device 102.

At operation 402, the interrogation device 104 interacts with, and establishes communication with, the sensing device 102. In some examples, the interrogation device 104 and the sensing device 102 is connected via the wireless communication link 108. An example of the communication is discussed above in more detail.

At operation 404, the interrogation device 104 determines whether a user of the interrogation device 104 has been authenticated. If it is determined that no authentication has been performed with the interrogation device 104 ("NO" at operation 404), the method 400 moves on to operation 406. Otherwise ("YES" at operation 404), the method 400 continues at operation 414.

At operation 406, the interrogation device 104 transmits a request for the non-patient specific data 170 to the sensing device 102. Once receiving the request, the sensing device 102 retrieves and transmits at least a portion of the non-patient specific data 170 to the interrogation device 104. In some examples, only a portion of the non-patient specific data 170 can be selected and transmitted based on the request. In other examples, the entire non-patient specific data 170 saved in the sensing device 102 can be transmitted to the interrogation device 104. At operation 408, the interrogation device 104 receives the non-patient specific data 170 from the sensing device 102. Then, at operation 410, the interrogation device 104 presents at least a portion of the transmitted non-patient specific data 170 thereon so that the user of the interrogation device 104 is informed of such data. The non-patient specific data 170 can be presented to the user through the user interface 224 of the interrogation device 104. Examples of the user interface 224 with such data are illustrated with reference to FIGS. 14 and 15.

If it is determined that authentication has been performed with the interrogation device 104 ("YES" at operation 404), at operation 414, the interrogation device 104 determines a level of authentication that the user has provided with the interrogation device 104. As described herein, the level of authentication is used to determine data that is selected from the sensing device data 106 and presented on the interrogation device 104. In some examples, the data is selected from the patient specific data 172 based on the level authentication. In other examples, at least a portion of the data can also be selected from the non-patient specific data 170.

At operation 416, once the level of authentication is determined, the interrogation device 104 sends to the sensing device 102 a request for data corresponding to the level of authentication. Upon receiving the request, the sensing device 102 retrieves and transmits the requested data to the interrogation device 104. At operation 418, the interrogation device 104 receives the requested data from the sensing device 102. Then, at operation 420, the interrogation device 104 presents at least a portion of the transmitted data thereon so that the user of the interrogation device 104 is informed of such data. For examples, the transmitted data can be presented to the user through the user interface 224 of the interrogation device 104. Examples of the user interface 224 with such data are illustrated with reference to FIGS. 16 and 17.

Figure 9:
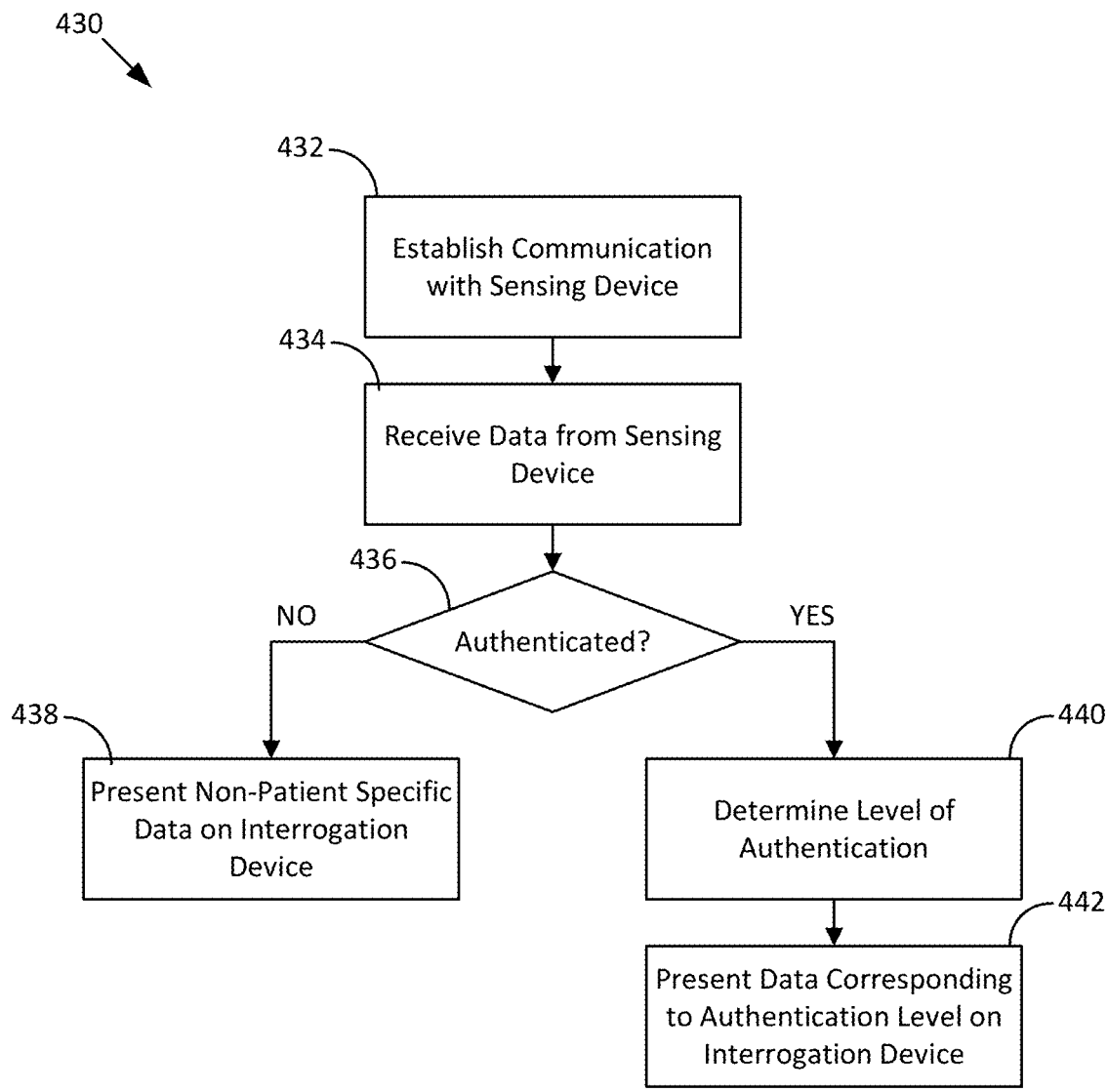
FIG. 9 is a flowchart illustrating another example method of operating the interrogation device in connection with the sensing device.

FIG. 9 is a flowchart illustrating another example method 430 of operating the interrogation device 104 in connection with the sensing device 102.

At operation 432, the interrogation device 104 interacts with, and establishes communication with, the sensing device 102. In some examples, the interrogation device 104 and the sensing device 102 is connected via the wireless communication link 108. The communication between the interrogation device 104 and the sensing device 102 is established similarly to the communication established in the operation 402 in FIG. 8.

At operation 434, once the communication has been established, the sensing device 102 transmits the sensing device data 106 to the interrogation device 104, and the interrogation device 104 receives the data 106 from the sensing device 102.

At operation 436, the interrogation device 104 determines whether a user of the interrogation device 104 has been authenticated. If it is determined that no authentication has been performed with the interrogation device 104 ("NO" at operation 436), the method 430 moves on to operation 438. Otherwise ("YES" at operation 436), the method 430 continues at operation 440.

At operation 438, the interrogation device 104 presents at least a portion of the non-patient specific data 170 to inform the user of the interrogation device 104 of such data. For example, if there is no authentication performed with the interrogation device 104, the interrogation device 104 selects the non-patient specific data 170 from the transmitted sensing device data 106, which do not require user authentication to be disclosed to the user of the interrogation device 104. The selected data 170 is presented on the interrogation device 104 in various manners, such as through the user interface 224, as described in more detail with reference to FIGS. 14 and 15.

At operation 440, if any authentication is found to have been performed with the interrogation device 104, the interrogation device 104 determines a level of authentication that has been verified with the interrogation device 104. The level of authentication is used to determine data that is selected from the transmitted sensing device data 106 to the interrogation device 104. In some examples, the data is selected from the patient specific data 172 based on the level authentication. In other examples, at least a portion of the data can also be selected from the non-patient specific data 170. At operation 442, once the level of authentication is determined, the interrogation device 104 presents at least a portion of the data corresponding to the determined level of authentication. For examples, the data can be presented to the user through the user interface 224 of the interrogation device 104. Examples of the user interface 224 with such data are illustrated with reference to FIGS. 16 and 17.

Figure 10:
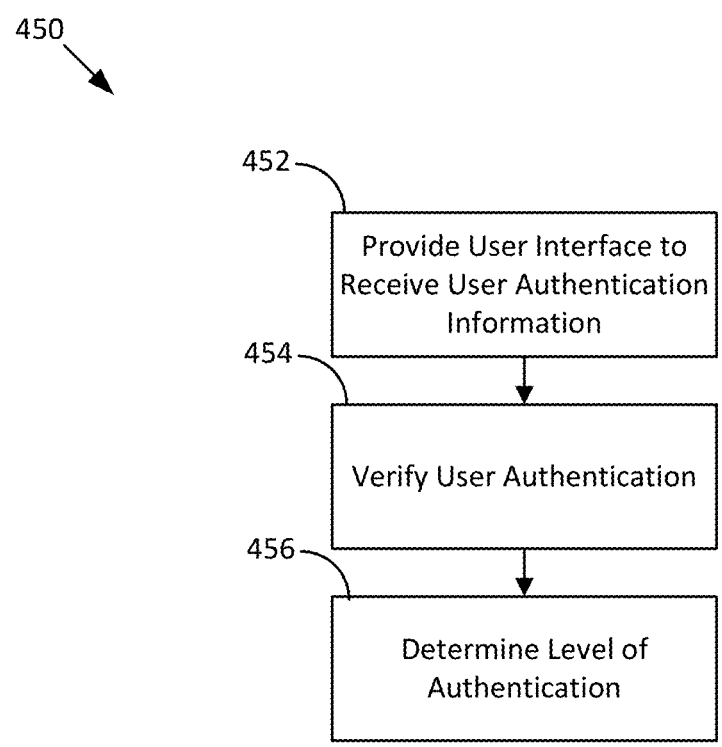
FIG. 10 is a flowchart illustrating an example method for operating the interrogation device for user authentication.

FIG. 10 is a flowchart illustrating an example method 450 for operating the interrogation device 104 for user authentication.

At operation 452, the interrogation device 104 provides the user interface 224 to receive user authentication information. In some examples, the user of the interrogation device 104 can input authentication information to the interrogation device 104 via the user interface 224. Examples of authentication information include a set of user identification (ID) and password, and a security code that is provided to the user in various manners. Examples of the user interface 224 are illustrated with reference to FIGS. 12 and 13.

In other examples, authentication information can be automatically retrieved from data that is stored in the interrogation device 104. For examples, where the interrogation device 104 is implemented with a mobile computing device, information stored in the mobile device to identify the user can be used to authenticate the user in using the mobile computing device as the interrogation device 104.

At operation 454, the interrogation device 104 verifies the user authentication information provided by the user. In some examples, the interrogation device 104 stores data that contain user authentication reference information, which can be used to verify the information that is entered through the user interface of the interrogation device.

At operation 456, the interrogation device 104 determines a level of authentication. The user of the interrogation device 104 can be authenticated at different levels, and the level of authentication determines the extent and/or type of information that is to be selected from the sensing device data 106 and presented on the interrogation device 104 for user's review.

In this document, it is primarily described that a user of the interrogation device 104 is authenticated. Alternatively or in addition, it is also possible that the interrogation device 104 is authenticated in other examples.

Figure 11:
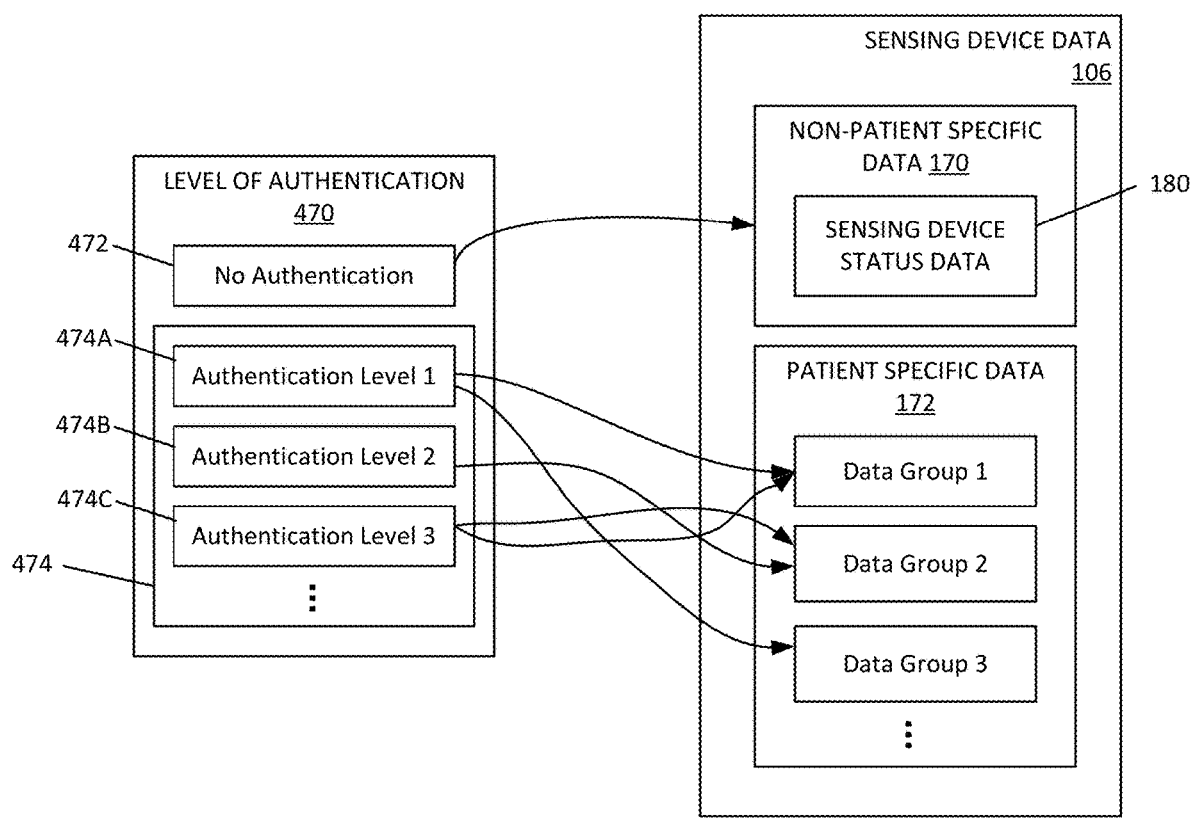
FIG. 11 schematically illustrates an example classification of authentication levels in connection with the sensing device data.

FIG. 11 schematically illustrates an example classification of authentication levels 470 in connection with the sensing device data 106. In some examples, the levels of authentication 470 are classified as no-authentication 472 and one or more different authentication levels 474 (such as 474A, 474B, and 474B). In the illustrated example, three authentication levels 474A, 474B, and 474B are illustrated. In other examples, different numbers of authentication levels are possible.

The no-authentication 472 indicates that authentication has not been performed or verified with the interrogation device 104. For example, when a user of the interrogation device 104 does not provide user authentication information via the interrogation device 104, or when the information provided by the user is not verified, it is determined that no authentication is performed with the interrogation device 104.

When no authentication is verified, information accessible via the interrogation device 104 is limited to the non-patient specific data 170. In some examples, when there is no user authentication, the interrogation device 104 displays only the non-patient specific data 170 or a portion thereof (such as the sensing device status data 180) via the user interface 224.

Other authentication levels 474 are determined based on user authentication information provided by the user. In some examples, the interrogation device 104 includes rule data that correlates particular user authentication information to a particular level of user authentication.

The data that is accessible via the interrogation device 104 is determined based on the authentication level 474. In some examples, the interrogation device 104 includes rule data that is used to select information from the sensing device data 106 for presenting on the interrogation device 104, based on the level of user authentication. In the illustrated example, when a user of the interrogation device 104 is authenticated as Authentication Level 1 474A, only data groups 1 and 3 are accessible via the interrogation device 104 and disclosed to the user. When the user is found to have Authentication Level 2 474B, the interrogation device 104 can display data groups 2. When Authentication Level 3 474C is determined, the interrogation device 104 can only present data groups 1 and 2.

Figure 12:
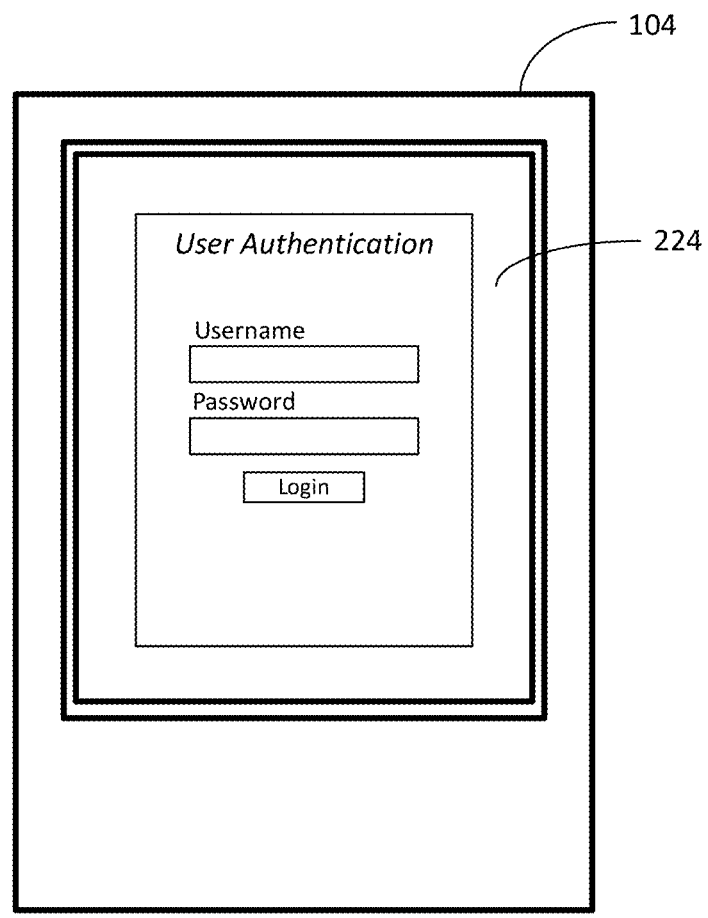
FIG. 12 schematically illustrates an example user interface for receiving user authentication information via the interrogation device.
Figure 13:
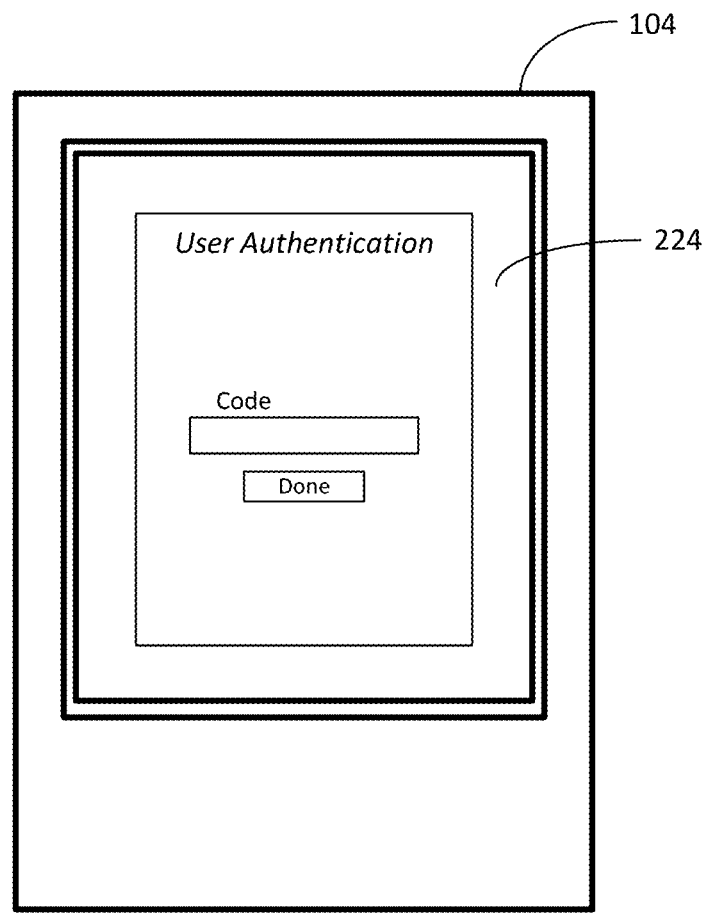
FIG. 13 schematically illustrates another example user interface for receiving user authentication information via the interrogation device.

FIGS. 12 and 13 schematically illustrate examples of the user interface 224 for receiving user authentication information via the interrogation device 104. In FIG. 12, the user interface 224 is presented on a display screen of the interrogation device 104 and configured to enable the user to input a username and a password as user authentication. In FIG. 13, the user interface 224 is configured to prompt the user to enter a code to verify the user's authentication.

Figure 14:
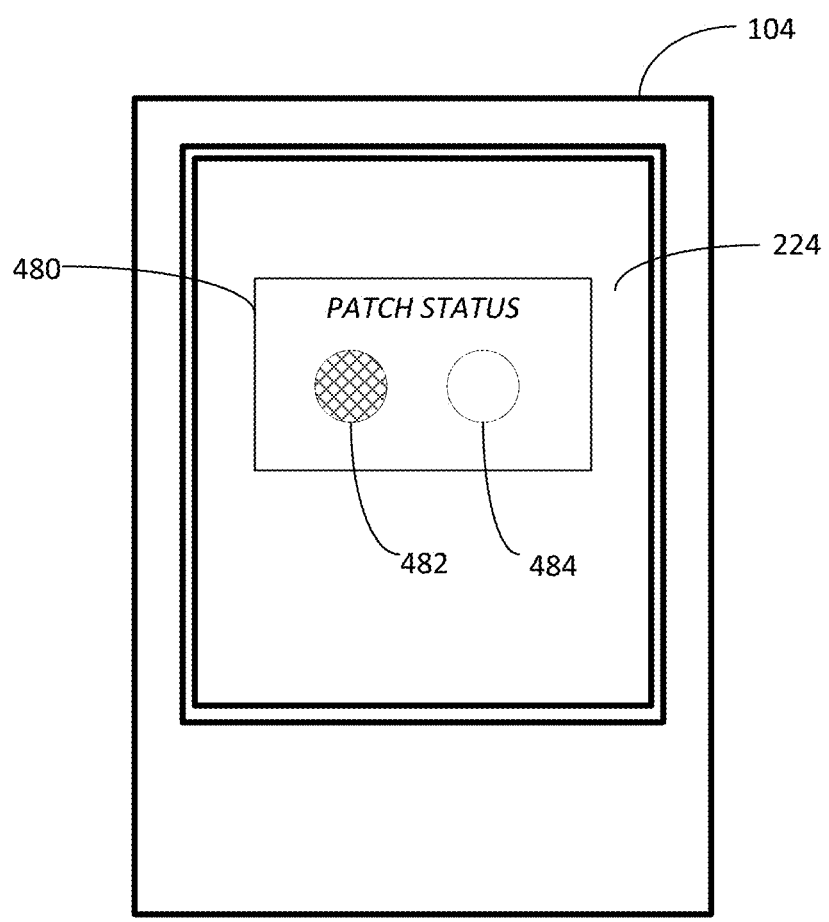
FIG. 14 schematically illustrates an example user interface for displaying information without user authentication.
Figure 15:
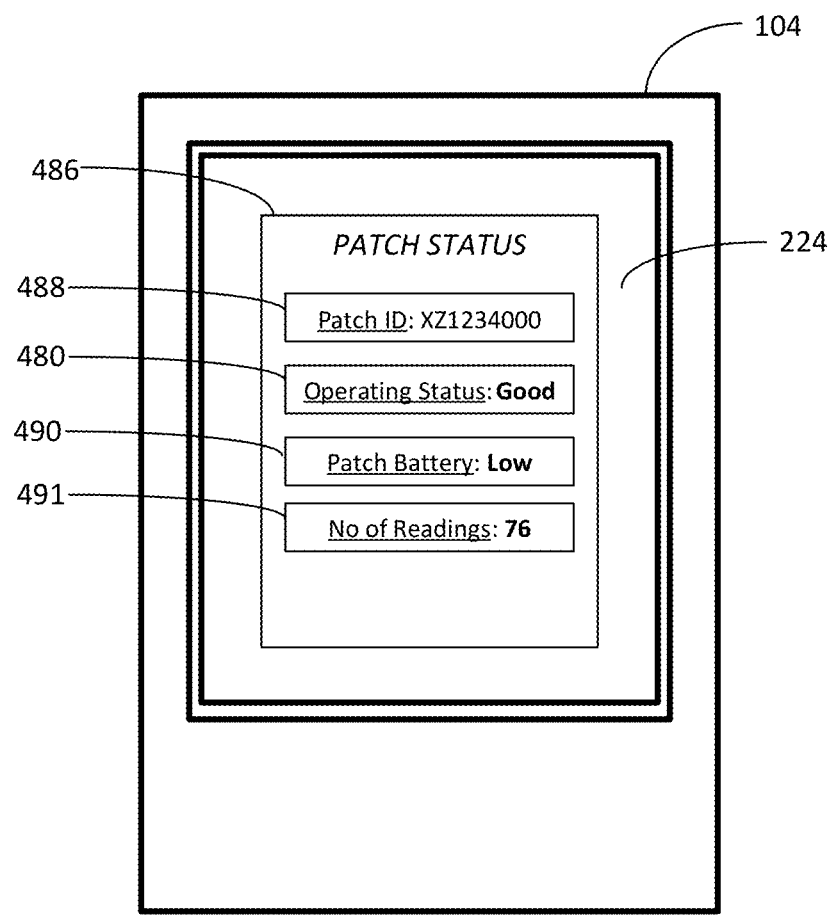
FIG. 15 schematically illustrates another example user interface for displaying information without user authentication.

FIGS. 14 and 15 schematically illustrate example of the user interface 224 for displaying information without user authentication. As described herein, when no authentication is verified with the interrogation device 104, the interrogation device 104 is configured to present at least a portion of the non-patient specific data 170 to the user of the interrogation device 104.

In some examples, as shown in FIG. 14, the interrogation device 104 displays the operating status 480 of the sensing device in a simple, intuitive manner. The user interface 224 of the interrogation device 104 is configured to use a color indication to represent whether the interrogation device 104 is in operation as desired. For example, a first color 482 (e.g., green) is turned on to indicate that the interrogation device 104 is appropriately operating, while a second color 484 (e.g., red) is turned off. In contrast, when the interrogation device 104 is not determined to be operating properly, the second color 484 is turned on and the first color 482 is turned off. In some examples, such different colors can be digitally implemented with a display device (such as the display device 340 as shown in FIG. 7). In other examples, the interrogation device 104 includes one or more lighting devices (e.g., LED light bulbs) for implementing one or more colors. Other configurations are also possible in yet other examples.

In other examples, as shown in FIG. 15, the interrogation device 104 displays information about the sensing device status 486. The user interface 224 of the interrogation device 104 displays various pieces of information selected from the non-patient specific data 170. Examples of such information include the identification information 488 for the sensing device 102, the operating status 480 of the sensing device 102, the level of battery 490 remaining in the sensing device 102, and a number of measurements performed and/or obtained by the sensing device 102.

Figure 16:
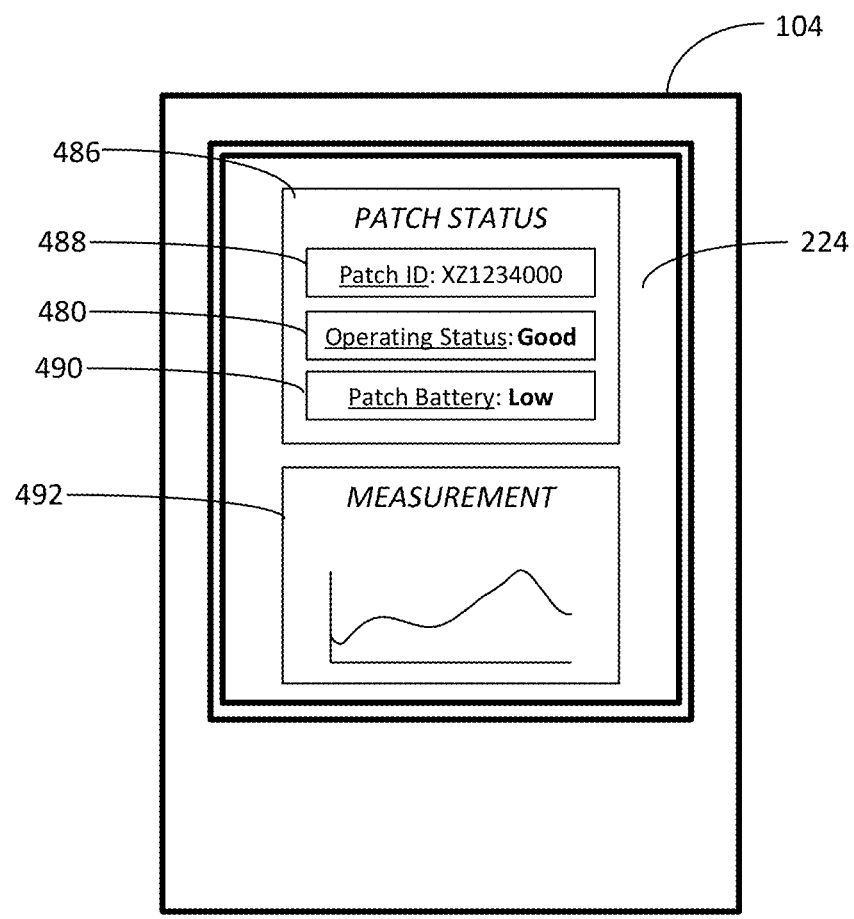
FIG. 16 schematically illustrates an example user interface for displaying information when a user of the interrogation device is authenticated.
Figure 17:
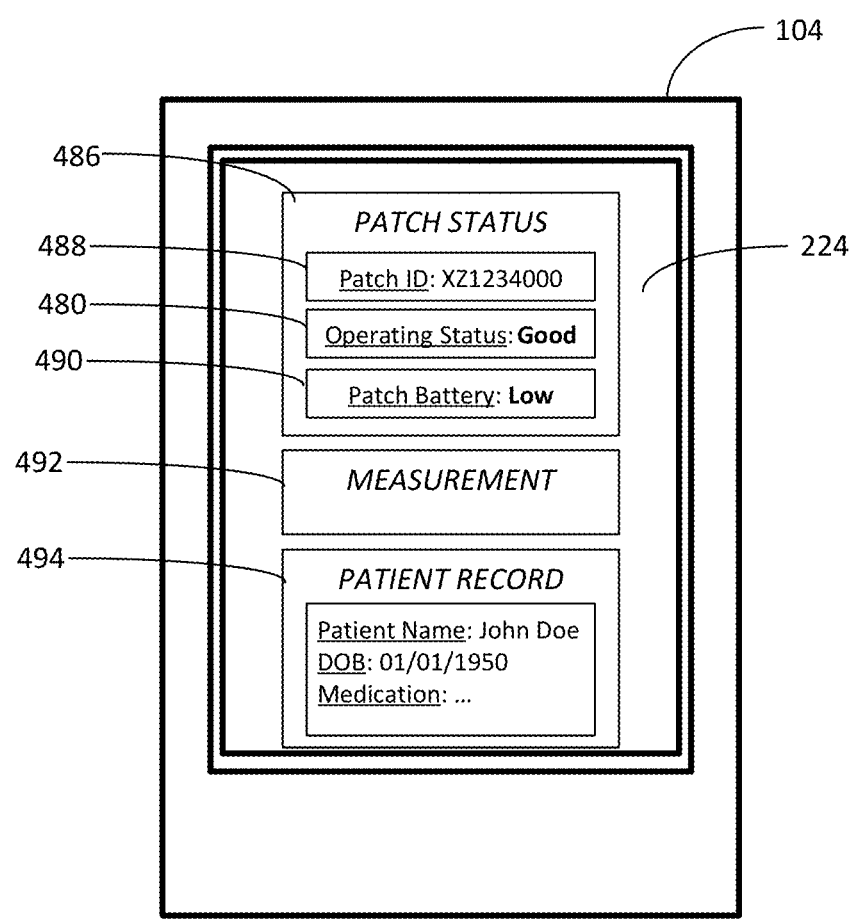
FIG. 17 schematically illustrates another example user interface for displaying information when a user of the interrogation device is authenticated.

FIGS. 16 and 17 schematically illustrate examples of the user interface 224 for displaying information when a user of the interrogation device 104 is authenticated. As described herein, when the user of the interrogation device 104 is authenticated, the interrogation device 104 is configured to present at least a portion of the patient specific data 172 depending on the level of authentication.

In some examples, as shown in FIG. 16, when the interrogation device 104 determines that the user has been authenticated as Authentication Level 1, the interrogation device 104 displays physiological parameter readings 492. The physiological parameter readings 492 can be presented in various formats, such as in a graph, chart, diagram, table, and/or text. In some examples, the interrogation device 104 also displays the sensing device status 486 (including, for example, the sensing device ID 488, the sensing device operating status 480, and the battery level 490), in addition to the physiological parameter readings 492.

In other examples, as shown in FIG. 17, when the interrogation device 104 determines that the user has been authenticated as Authentication Level 2, the interrogation device 104 displays a patient record 494 associated with the subject S, in addition to the physiological parameter readings 492 and/or the sensing device status 486.

As exemplified in FIGS. 16 and 17, the interrogation device 104 is configured to display different pieces of information selected from the patient specific data 172 in accordance with different levels of authentication.

The various examples and teachings described above are provided by way of illustration only and should not be construed to limit the scope of the present disclosure. Those skilled in the art will readily recognize various modifications and changes that may be made without following the example examples and applications illustrated and described herein, and without departing from the true spirit and scope of the present disclosure.

What is claimed is:

1. A system for monitoring a physiological parameter of a subject, the system comprising:
a sensing device engaged to a subject and configured to measure a physiological parameter of the subject; and
an interrogation device operable by a user and configured to:
establish communication with the sensing device;
receive data from the sensing device, the data including non-patient specific data;
determine whether the user is authenticated; and
present at least a portion of the non-patient specific data from the sensing device when the user is not authenticated, with the non-patient specific data including a status indicator providing an operational status of the sensing device to acquire the physiological parameter of the subject, the status indicator including:
a first state to indicate that the sensing device is functioning properly to acquire the physiological parameter of the subject; and
a second state to indicate that the sensing device is functioning improperly to acquire the physiological parameter of the subject.

2. The system of claim 1, wherein the interrogation device is further configured to:
provide a user interface configured to receive user authentication information;
when the user is authenticated, determine a level of authentication; and
present patient specific data corresponding to the level of authentication, the patient specific data transmitted from the sensing device.

3. The system of claim 2, wherein the patient specific data include at least one of physiological parameter data and a medical record associated with the subject.

4. The system of claim 1, wherein the interrogation device is further configured to transmit a trigger signal to the sensing device to activate the sensing device and establish the communication between the sensing device and the interrogation device.

5. The system of claim 1, wherein the interrogation device is configured to communicate with the sensing device via short range wireless communication.

6. The system of claim 1, wherein the non-patient specific data include information about a status of the sensing device.

7. The system of claim 6, wherein the status of the sensing device includes at least one of an operating status of the sensing device, a level of battery remaining in the sensing device, and a number of measurements obtained by the sensing device.

8. The system of claim 1, wherein the user of the interrogation device is the subject engaging the sensing device.

9. The system of claim 1, wherein the sensing device is configured as a body-worn patch removably attachable on a body surface of the subject.

10. The system of claim 1, wherein the sensing device is configured to periodically detect the physiological parameter of the subject for a monitoring period of time.

11. An interrogation apparatus for monitoring an operation of a physiological parameter sensing device, the interrogation apparatus comprising:
a processing device configured to control operation of the interrogation apparatus;
a display device; and
a computer readable data storage device storing software instructions that, when executed by the processing device, cause the interrogation apparatus to:
establish communication with the sensing device;
receive data from the sensing device, the data including non-patient specific data;
determine whether the user is authenticated; and
display at least a portion of the non-patient specific data from the sensing device using the display device when the user is not authenticated, with the non-patient specific data including a status indicator providing an operational status of the sensing device to acquire the physiological parameter of the subject, the status indicator including:
a first state to indicate that the sensing device is functioning properly to acquire the physiological parameter of the subject; and
a second state to indicate that the sensing device is functioning improperly to acquire the physiological parameter of the subject.

12. The apparatus of claim 11, wherein the software instructions further cause the apparatus to:
provide a user interface configured to receive user authentication information;
when the user is authenticated, determine a level of authentication; and
display patient specific data corresponding to the level of authentication using the display device, the patient specific data transmitted from the sensing device.

13. The apparatus of claim 12, wherein the patient specific data include at least one of physiological parameter data and a medical record associated with the subject.

14. The apparatus of claim 11, wherein the software instructions further cause the apparatus to:
transmit a trigger signal to the sensing device to activate the sensing device and establish the communication between the sensing device and the interrogation apparatus.

15. The apparatus of claim 11, wherein the software instructions further cause the apparatus to:
communicate with the sensing device via short range wireless communication.

16. The apparatus of claim 11, wherein the non-patient specific data include information about a status of the sensing device.

17. The apparatus of claim 16, wherein the status of the sensing device includes at least one of an operating status of the sensing device, a level of battery remaining in the sensing device, and a number of measurements obtained by the sensing device.

18. The apparatus of claim 11, wherein the user of the interrogation apparatus is the subject engaging the sensing device.

19. A method of monitoring an operation of a physiological parameter sensing device, the sensing device configured to detect a physiological parameter of a subject, the method comprising:
transmitting a trigger signal to the sensing device to activate the sensing device;
establishing communication with the sensing device;
providing a user interface configured to receive user authentication information;
determining whether the user is authenticated;
when the user is not authenticated,
receiving non-patient specific data from the sensing device, the non-patient specific data including a status indicator providing an operational status of the sensing device to acquire the physiological parameter of the subject; and
displaying at least a portion of the non-patient specific data using a display device, including:
activating a first indicator when the sensing device is functioning properly to acquire the physiological parameter of the subject; and
activating a second indicator when the sensing device is functioning improperly to acquire the physiological parameter of the subject; and
when the user is authenticated,
determining a level of authentication;
receiving patient-specific data corresponding to the level of authentication; and
displaying at least a portion of the patient specific data corresponding to the level of authentication.

20. The method of claim 19, wherein the non-patient specific data include information about a status of the sensing device.

* * * * *